United States Patent
Fiser et al.

(10) Patent No.: US 10,149,718 B2
(45) Date of Patent: Dec. 11, 2018

(54) CONVERTIBLE OPTICAL AND PRESSURE WAVE ABLATION SYSTEM AND METHOD

(71) Applicant: The Spectranetics Corporation, Colorado Springs, CO (US)

(72) Inventors: Richard Fiser, Monument, CO (US); Kenneth P. Grace, Woodland Park, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 105 days.

(21) Appl. No.: 14/735,946

(22) Filed: Jun. 10, 2015

(65) Prior Publication Data
US 2015/0359593 A1 Dec. 17, 2015

Related U.S. Application Data

(60) Provisional application No. 62/010,577, filed on Jun. 11, 2014.

(51) Int. Cl.
| | |
|---|---|
| *A61B 18/24* | (2006.01) |
| *A61B 18/00* | (2006.01) |
| *A61B 18/22* | (2006.01) |
| *A61B 18/26* | (2006.01) |
| *A61N 7/02* | (2006.01) |

(52) U.S. Cl.
CPC ............ *A61B 18/24* (2013.01); *A61B 18/245* (2013.01); *A61B 2018/00345* (2013.01); *A61B 2018/00577* (2013.01); *A61B 2018/00994* (2013.01); *A61B 2018/2266* (2013.01); *A61B 2018/266* (2013.01); *A61N 7/022* (2013.01)

(58) Field of Classification Search
CPC ........ A61N 7/22; A61B 18/24; A61B 18/245; A61B 2018/345; A61B 2018/577; A61B 2018/994; A61B 2018/2266; A61B 2018/266
USPC ............................................ 606/11
See application file for complete search history.

(56) References Cited

U.S. PATENT DOCUMENTS

| | | | | |
|---|---|---|---|---|
| 4,913,142 A | * | 4/1990 | Kittrell | A61B 1/00096 606/15 |
| 5,254,112 A | * | 10/1993 | Sinofsky | A61B 5/02007 600/439 |
| 2005/0131289 A1 | * | 6/2005 | Aharoni | A61B 5/02007 600/407 |
| 2009/0312673 A1 | * | 12/2009 | Thapliyal | A61B 18/00 601/2 |

* cited by examiner

*Primary Examiner* — John R Downey
*Assistant Examiner* — Vynn Huh (57) ABSTRACT

The present disclosure relates to a system and method for providing laser energy through a catheter towards a second end portion of the catheter. Based on a characteristic of the laser energy multiple types of ablation therapy may be implemented. A first ablation therapy is directed at the target site when the laser energy at the second end portion of the laser energy delivery system has a first characteristic. A second ablation therapy is directed at the target site when the laser energy at the second end portion of the laser energy delivery system has a second characteristic. The first ablation therapy may be an optical ablation therapy wherein the laser energy is directed at the target site as optical energy and the second ablation therapy may be a pressure wave ablation therapy wherein pressure waves are directed at the target site as pressure wave energy.

16 Claims, 6 Drawing Sheets

CONVERTIBLE OPTICAL AND PRESSURE WAVE ABLATION SYSTEM AND METHOD

CROSS-REFERENCE TO RELATED APPLICATION

The present application claims the benefit of and priority to, under 35 U.S.C. § 119(e), U.S. Provisional Application Ser. No. 62/010,577, filed Jun. 11, 2014, entitled CONVERTIBLE OPTICAL AND PRESSURE WAVE ABLATION SYSTEM AND METHOD, which is hereby incorporated by reference in its entirety for all purposes.

FIELD OF THE DISCLOSURE

The present disclosure relates generally to a method and system for delivering energy capable of ablating tissue to a target site, and more specifically to a method and system for providing multiple types of ablation energy to a target site.

BACKGROUND

Human blood vessels often become occluded or blocked by plaque, thrombi, other deposits, or emboli which reduce the blood carrying capacity of the vessel. If the blockage occurs at a critical place in the circulatory system, serious and permanent injury can occur. Medical intervention, such as an angioplasty, is usually performed when significant occlusion is detected. For example, laser based catheter devices are often used to ablate the occlusions in the vessels.

Treatment of vascular lesions is made difficult by lesion morphology that can contain a variety of plaque types ranging from soft to bone hard. Different atherectomy tools have been developed to deal with different types of plaque. Performance with one plaque type is typically sacrificed for improved capability with another plaque type.

SUMMARY

According to an exemplary embodiment of the present disclosure, an ablation system for ablating a target site is provided. The ablation system comprising a laser source operative to provide laser energy and a laser energy delivery device operatively coupled to the laser source on a first end portion. The laser energy delivery device being operative to transport the laser energy produced by the laser source from the first end portion towards a second end portion. The laser energy delivery device directing a first ablation therapy at the target site when the laser energy at the second end portion of the laser energy delivery device has a first characteristic and directing a second ablation therapy at the target site when the laser energy at the second end portion of the laser energy delivery device has a second characteristic. In an example thereof, the first ablation therapy is an optical ablation therapy wherein the laser energy is directed at the target site as optical energy. In another example thereof, the second ablation therapy is a pressure wave ablation therapy wherein pressure waves are directed at the target site as pressure wave energy. In yet another example thereof, the first ablation therapy is an optical ablation therapy wherein the laser energy is directed at the target site as optical energy and the second ablation therapy is a pressure wave ablation therapy wherein pressure waves are directed at the target site as pressure wave energy. In a variation thereof, the first characteristic is a first polarization state and the second characteristic is a second polarization state. In still another example thereof, the first characteristic is a first polarization state and the second characteristic is a second polarization state. In a variation thereof, the ablation system further comprises a polarization module supported by one of the laser source and the laser energy delivery device. The polarization module controlling a polarization state of the laser energy delivered to the second end portion of the laser energy delivery device. In a refinement thereof, the polarization module has a first setting wherein the polarization state of the laser energy delivered to the second end portion of the laser energy delivery device is the first polarization state and a second setting wherein the polarization state of the laser energy delivered to the second end portion of the laser energy delivery device is the second polarization state. In a further refinement thereof, the polarization module has a third setting wherein the polarization state of the laser energy delivered to the second end portion of the laser energy delivery device is a third polarization state. In still a further refinement thereof, when the polarization state of the laser energy delivered to the second end portion of the laser energy delivery device is the third polarization state the laser energy delivery device directs the first ablation therapy at the target site as optical energy and directs the second ablation therapy at the target site as pressure wave energy. In still a further refinement thereof, the first ablation therapy is an optical ablation therapy wherein the laser energy is directed at the target site as optical energy and the second ablation therapy is a pressure wave ablation therapy wherein pressure waves are directed at the target site as pressure wave energy. In another variation, the first ablation therapy is an optical ablation therapy wherein the laser energy is directed at the target site as optical energy and the second ablation therapy is a pressure wave ablation therapy wherein pressure waves are directed at the target site as pressure wave energy.

In another exemplary embodiment of the present disclosure, a catheter assembly for an ablation system is provided. The catheter system receiving laser energy from a laser source. The catheter assembly comprising at least one transport member having a first end and a second end; a coupler positioned proximate the first end of the at least one transport member, the coupler adapted to couple laser energy from the laser source into the at least one transport member; and at least one transducer coupled proximate the second end of the at least one transport member. The at least one transducer passes the laser energy out of the catheter assembly as optical energy when the laser energy has a first characteristic and converts the laser energy to pressure wave energy when the laser energy has a second characteristic. In an example thereof, the first characteristic is a first polarization state and the second characteristic is a second polarization state. In a variation thereof, the at least one transducer absorbs laser energy with the second polarization state. In another variation thereof, when the first characteristic is a third polarization state, a first component of the laser energy is passed out of the catheter assembly as optical energy and a second component of the laser energy is converted to pressure wave energy. In another example, the at least one transducer has a face from which the pressure wave energy emanates. In a variation thereof, the face has a continuous profile. In a refinement thereof, the face has a concave profile. In another variation thereof, the face has a convex profile. In still another variation thereof, the face has a linear profile. In still another example, the face has a stepped profile. In a variation thereof, the face has a continuous profile. In a refinement thereof, the face has a concave profile. In another variation thereof, the face has a convex profile. In still another variation thereof, the face has a linear profile. In yet another variation thereof, the stepped profile is created by a first transport member having a second end surface which is recessed relative to a second end surface of a second transport member.

In yet another exemplary embodiment of the present disclosure, a tissue ablation method is provided. The tissue ablation method comprising sending laser energy through a laser energy delivery device towards a second end portion of the laser energy delivery device; directing a first ablation therapy at the target site when the laser energy at the second end portion of the laser energy delivery device has a first characteristic; and directing a second ablation therapy at the target site when the laser energy at the second end portion of the laser energy delivery device has a second characteristic.

According to another exemplary embodiment of the present disclosure, a non-transitory computer-readable medium contains instructions that, when executed, cause one or more processors to perform a method that includes sending laser energy through a laser energy delivery device towards a second end portion of the laser energy delivery device; directing a first ablation therapy at the target site when the laser energy at the second end portion of the laser energy delivery device has a first characteristic; and directing a second ablation therapy at the target site when the laser energy at the second end portion of the laser energy delivery device has a second characteristic.

In still another exemplary embodiment, a tissue ablation method for an ablation system capable of administering a plurality of types of ablation therapy is provided. The method comprising receiving a request for a first type of ablation therapy of the plurality of types of ablation therapy; and altering a polarization state of optical energy produced by a laser source to provide the energy for the first type of ablation therapy, the plurality of ablation therapies including at least one optical energy therapy and at least one pressure wave energy therapy. In one example, the first type of ablation therapy is a pressure wave energy therapy. In another example, the first type of ablation therapy is an optical energy therapy.

According to another exemplary embodiment of the present disclosure, a non-transitory computer-readable medium contains instructions that, when executed, cause one or more processors to perform a method that includes receiving a request for a first type of ablation therapy of the plurality of types of ablation therapy; and altering a polarization state of optical energy produced by a laser source to provide the energy for the first type of ablation therapy, the plurality of ablation therapies including at least one optical energy therapy and at least one pressure wave energy therapy. In one example, the first type of ablation therapy is a pressure wave energy therapy. In another example, the first type of ablation therapy is an optical energy therapy.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

A "catheter" is a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter). A "laser catheter" is a catheter that includes optical fibers capable of transmitting laser light.

A "coupler" or "fiber optic coupler" refers to the optical fiber device with one or more input fibers and one or several output fibers. Fiber couplers are commonly special optical fiber devices with one or more input fibers for distributing optical signals into two or more output fibers. Optical energy is passively split into multiple output signals (fibers), each containing light with properties identical to the original except for reduced amplitude. Fiber couplers have input and output configurations defined as M×N. M is the number of input ports (one or more). N is the number of output ports and is always equal to or greater than M. Fibers can be thermally tapered and fused so that their cores come into intimate contact. This can also be done with polarization-maintaining fibers, leading to polarization-maintaining couplers (PM couplers) or splitters. Some couplers use side-polished fibers, providing access to the fiber core. Couplers can also be made from bulk optics, for example in the form of microlenses and beam splitters, which can be coupled to fibers ("fiber pig-tailed").

The term "logic" or "control logic" as used herein may include software and/or firmware executing on one or more programmable processors, application-specific integrated circuits (ASICs), field-programmable gate arrays (FPGAs), digital signal processors (DSPs), hardwired logic, or combinations thereof. Therefore, in accordance with the embodiments, various logic may be implemented in any appropriate fashion and would remain in accordance with the embodiments herein disclosed.

The term "computer-readable medium" as used herein refers to any storage and/or transmission medium that participate in providing instructions to a processor for execution. Such a medium is commonly tangible and non-transient and can take many forms, including but not limited to, non-volatile media, volatile media, and transmission media and includes without limitation random access memory ("RAM"), read only memory ("ROM"), and the like. Non-volatile media includes, for example, NVRAM, or magnetic or optical disks. Volatile media includes dynamic memory, such as main memory. Common forms of computer-readable media include, for example, a floppy disk (including without limitation a Bernoulli cartridge, ZIP drive, and JAZ drive), a flexible disk, hard disk, magnetic tape or cassettes, or any other magnetic medium, magneto-optical medium, a digital video disk (such as CD-ROM), any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. Computer-readable storage medium commonly excludes transient storage media, particularly electrical, magnetic, electromagnetic, optical, magneto-optical signals.

A "laser emitter" as used herein refers to an end portion of a fiber or an optical component that emits laser light from a distal end of the catheter towards a desired target, which is typically tissue.

An optical fiber (or laser active fibre) as used herein refers to a flexible, transparent fiber made of an optically transmissive material, such as glass (silica) or plastic, which functions as a waveguide, or "light pipe", to transmit light between the two ends of the fiber.

A "polarization-maintaining" or a "polarization-preserving" optical fiber as used herein refers to an optical fiber in which polarized light, such as polarized laser light, maintains polarization during transmission through the optical fiber and exits the optical fiber in the same polarization state.

Figure 1:
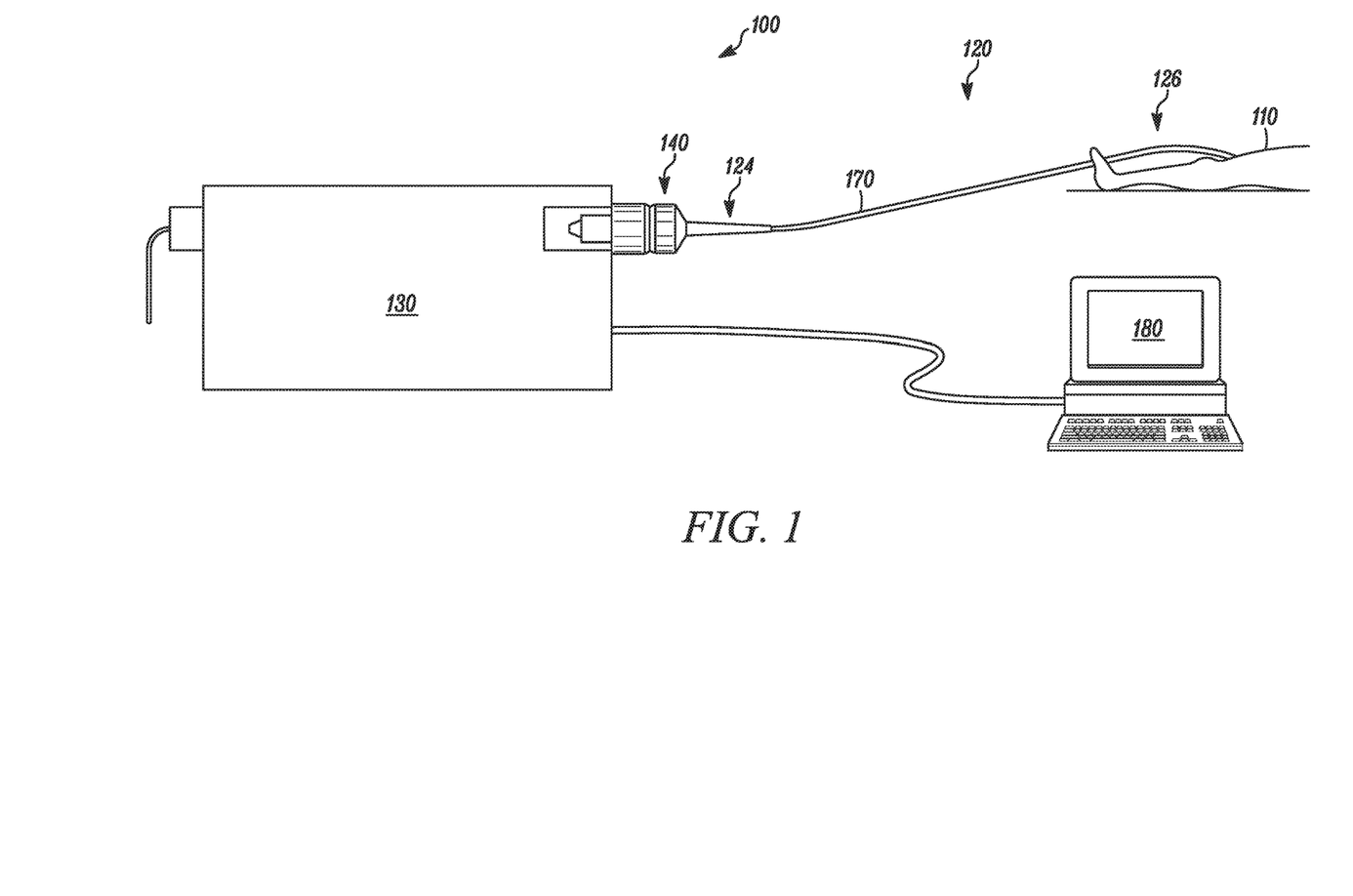
FIG. 1 illustrates an exemplary ablation system.

FIG. 1 illustrates an exemplary ablation system 100. Ablation system 100 includes a laser apparatus 130 coupled to a laser controller 180. Controller 180 includes one or more computing devices programmed to control laser 130, as described herein with reference to FIGS. 12 and 13. Controller 180 may be internal or external to laser apparatus 130. Laser apparatus 130 may include an excimer laser or another suitable laser. In some embodiments, laser 130 produces light in the ultraviolet frequency range. In one embodiment, laser 130 produces optical energy in pulses.

Laser 130 is connected with the proximal end of a laser energy delivery system 120, illustratively a laser catheter 170 via coupler 140. Laser catheter 170 includes one or more transport members which receive laser energy from laser 130 and transports the received laser energy from a first, proximal end 124 of laser energy catheter 170 towards a second, distal end 126 of laser catheter 170. The distal end of catheter 170 may be inserted into a vessel or tissue of a human body 110. In some embodiments, system 100 employs a plurality of light guides as the transport members, such as optical fibers, that guide laser light from laser 130 through catheter 170 toward a target area in human body 110. In some embodiments, optical fibers may be polarization-maintaining or polarization-preserving optical fibers.

Exemplary laser catheter devices or assemblies may include laser catheters and/or laser sheaths. Examples of laser catheters or laser sheath are sold by the Spectranetics Corporation under the tradenames ELCA™ and Turbo Elite™ (each of which is used for coronary intervention or catheterization such as recanalizing occluded arteries, changing lesion morphology, and facilitating stent placement) and SLSII™ and GlideLight™ (which is used for surgically implanted lead removal). The working (distal) end of a laser catheter typically has a plurality of laser emitters that emit energy and ablate the targeted tissue. The opposite (proximal) end of a laser catheter typically has a fiber optic coupler, which connects to a laser system or generator. One such example of a laser system is the CVX-300 Excimer Laser System, which is also sold by the Spectranetics Corporation.

Figure 2:
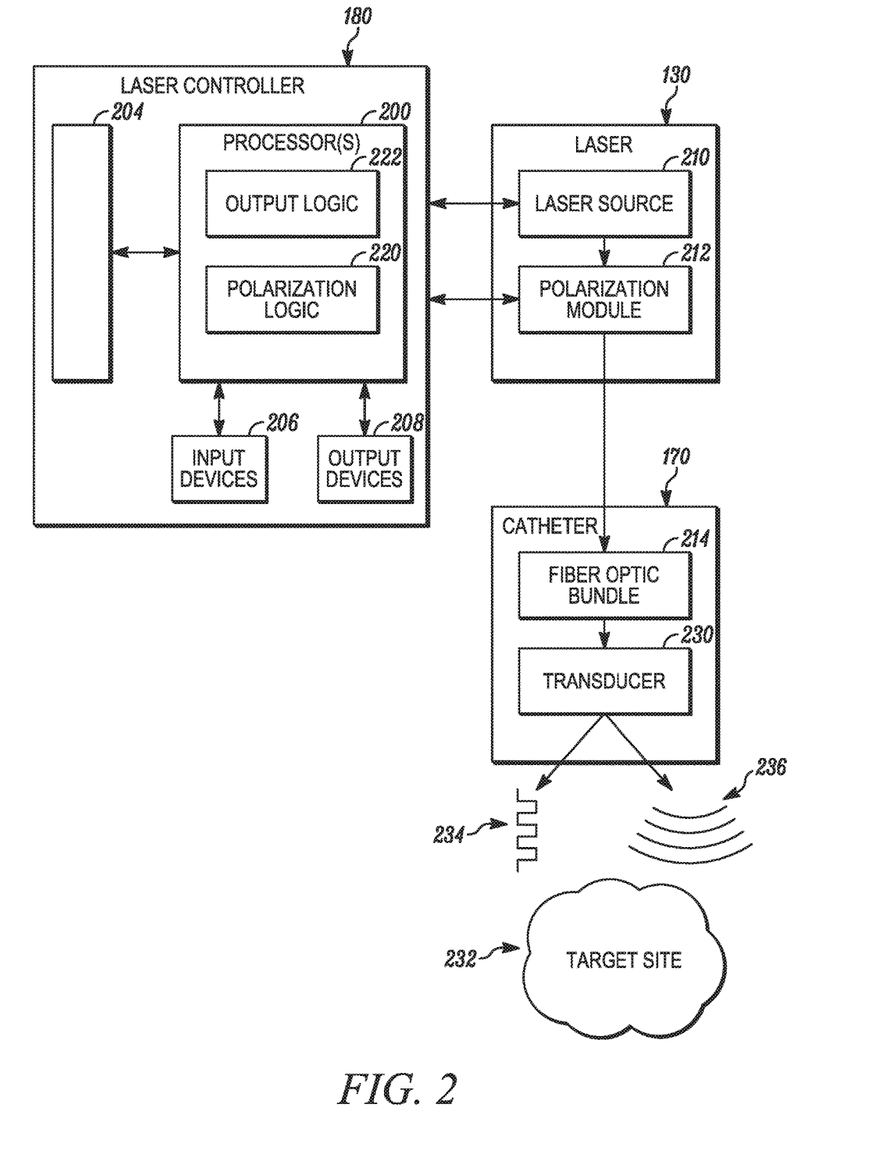
FIG. 2 illustrates a laser controller of the ablation system of FIG. 1 including output logic and polarization logic.

Referring to FIG. 2, laser controller 180 of FIG. 1 includes a non-transitory computer-readable medium (e.g., memory 204) that includes instructions that, when executed, cause one or more processors 200 to control laser 130 and/or other components of ablation system 100. Controller 180 includes one or more input devices 206 to receive input from an operator. Exemplary input devices include keys, buttons, touch screens, dials, switches, mouse, and trackballs which providing user control of laser 130. Controller 180 further includes one or more output devices 208 to provide feedback or information to an operator. Exemplary output devices include a display, lights, audio devices which provide user feedback or information.

A laser source 210 of laser 130 is operatively coupled to laser controller 180. Laser source 210 is operative to generate a laser signal or beam and provide the laser signal through a fiber optic bundle 214 of catheter 170 to the human. The laser energy passes through a polarization module 212 which polarizes the laser energy. Fiber optic bundle 214 serves as delivery devices for delivering the laser signal to the target area of the human.

Polarization module 212 polarizes the laser energy. In one embodiment, polarization module 212 is a linear polarizer which in a first orientation passes vertically polarized optical energy. If polarization module 212 is rotated to a second orientation then polarization module 212 passes horizontally polarized optical energy. Polarization module 212 may be rotated to a third position wherein polarization module 212 passes linearly polarized optical energy having both a vertically polarized component and a horizontally polarized component. In one embodiment, polarization module 212 provides circularly polarized light. In one embodiment, polarization module 212 provides elliptically polarized light.

In one embodiment, polarization module 212 is a linear polarizer and is manually actuatable by an operator to rotate polarization module 212 to a desired position. In another embodiment, polarization module 212 is a linear polarizer which is rotated under the control of laser controller 180. Polarization module 212 may include a plurality of polarizers which are individually moved in and out of the optical energy produced by laser source 210 either manually or under the control of laser controller 180. In one embodiment, polarization module 212 is part of laser apparatus 130 and is supported by laser apparatus 130. In one embodiment, polarization module 212 is part of laser catheter 170 and is supported by laser catheter 170. In one embodiment, polarization module 212 is part of coupler 140 and is supported by either laser apparatus 130 or laser catheter 170.

In the illustrated embodiment, processors 200 of laser controller 180 include polarization logic 220 which controls polarization module 212 to position polarization module 212 in a desired orientation or otherwise provide a desired polarization to the optical energy produced by laser source 210. Processors 200 also includes output logic 222 which controls laser apparatus 130 to control at least one of a pulse rate, a power level, and other characteristics of the optical energy output by laser source 210.

Exemplary polarization modules 212 may include wire grid polarizers, crystalline polarizers, elongated silver nanoparticles, polarizing beamsplitters, Brewster angle plates, birefringent materials (including plastic and crystalline), and liquid crystals. Wire grid polarizers are typically manufactured through lithographic metal deposition on a glass surface (such as the catheter tip). Crystalline polarizers are materials which include herapathite (polaroids are plastic sheets with embedded herapathite crystals. In one embodiment, polarization module 212 is part of laser source 210 which uses non-linear wavelength conversion crystals (which typically produce a polarized output).

Additional details of an exemplary laser apparatus 130 are described in U.S. Pat. No. 5,383,199, filed Jul. 2, 1992, entitled "Apparatus and Method for Optically Controlling the Output Energy of a Pulsed Laser Source," the entire disclosure of which is incorporated by reference herein. Additional details of exemplary catheters 170 are described in U.S. Pat. No. 8,545,488, filed Dec. 30, 2009, entitled "Cardiovascular Imaging System," the entire disclosure of which is incorporated by reference herein.

Returning to FIG. 2, laser catheter 170 further includes a transducer 230. Transducer 230 receives the optical energy that travels through fiber optic bundle 214 and either passes the optical energy on to a target site 232 as optical energy 234 or converts the optical energy to pressure wave energy 236. Exemplary pressure wave energy includes ultrasonic pulses. In one embodiment, transducer 230 is configured to focus one or both of the optical energy 234 and pressure wave energy 236.

In one embodiment, transducer 230 is a polarized absorbing material coupled to the end portion 126 of laser catheter 170. In one embodiment, transducer 230 is a polarized absorbing material coating applied to the end portion 126 of laser catheter 170. In one embodiment, transducer 230 is a polarized absorbing material embedded within laser catheter 170. Exemplary polarized absorbing materials include wire grid polarizers, crystalline polarizers, and elongated silver nanoparticles. Wire grid polarizers are typically manufactured through lithographic metal deposition on a glass surface (such as the catheter tip). Crystalline polarizers are materials which include herapathite (polaroids are plastic sheets with embedded herapathite crystals).

Figure 3:
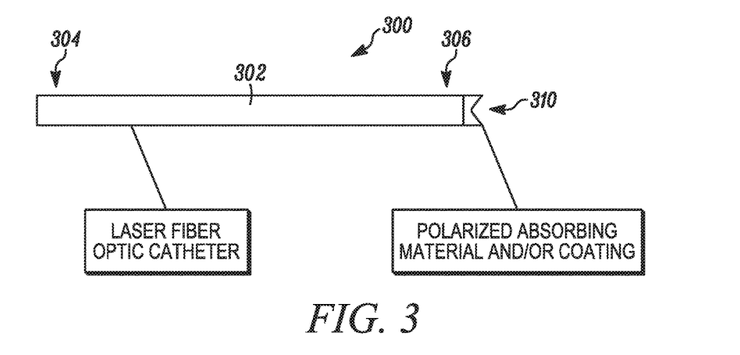
FIG. 3 illustrates an exemplary catheter of the ablation system of FIG. 1 including a distal transducer.
Figure 4:
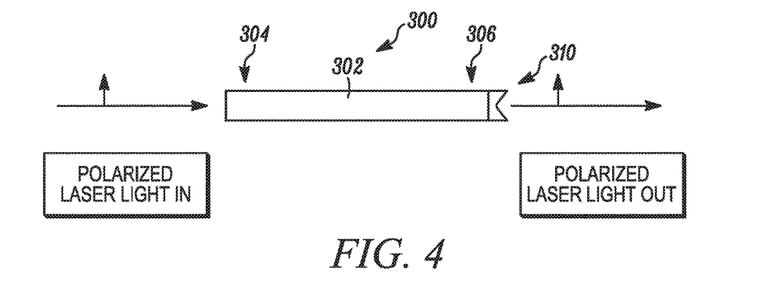
FIG. 4 illustrates the output of the exemplary catheter of FIG. 3 in response to receiving laser energy having a first polarization state.
Figure 5:
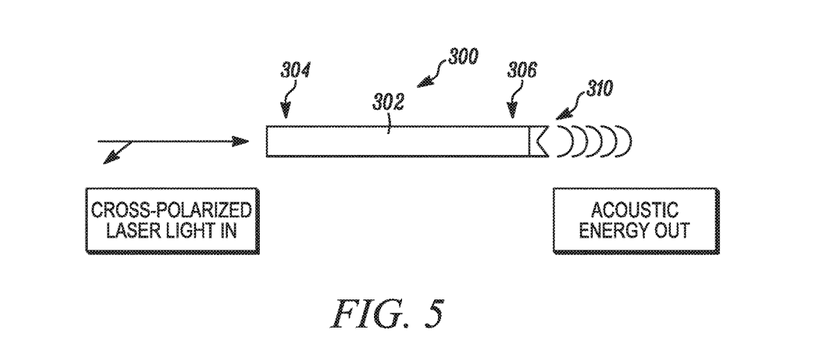
FIG. 5 illustrates the output of the exemplary catheter of FIG. 3 in response to receiving laser energy having a second polarization state.

Referring to FIGS. 3-5, an exemplary laser catheter 300 is provided. Laser catheter 300 includes one or more transport members 302 which transport optical energy from a first end 304 of the transport member 302 towards a second end 306 of the transport member 302. Coupled to second end 306 of laser catheter 300 is a polarized absorbing material 310. Exemplary polarized absorbing material 310 are provided herein.

In the embodiment illustrated in FIGS. 3-5, polarized absorbing material 310 is a linear polarized material which absorbs horizontally polarized optical energy. As shown in FIG. 4, when the optical energy traveling in laser catheter 300 is vertically polarized, polarized absorbing material 310 does not absorb the optical energy, but rather passes the optical energy out of laser catheter 300 as optical energy. As shown in FIG. 5, when the optical energy traveling in laser catheter 300 is horizontally polarized, polarized absorbing material 310 absorbs the optical energy. This absorption of the optical energy is changed into a pressure wave in the environment surrounding polarized absorbing material 310 due to the change in size of polarized absorbing material 310. In one embodiment, laser source 210 outputs a pulsed optical signal which results in a plurality of spaced apart pressure waves in the environment surrounding polarized absorbing material 310.

In one embodiment, the polarization of the optical energy traveling through laser catheter 300 results in both optical energy being passed into the environment surrounding polarized absorbing material 310 and is changed into a pressure wave in the environment surrounding polarized absorbing material. Thus, multiple types of therapy may be provided simultaneously.

In one embodiment, output logic 222 of laser controller 180 uses a first power level when optical energy is to be used as an ablation therapy and a second power level when pressure wave energy is to be used as an ablation therapy, the second power level being different from the first power level. In one embodiment, output logic 222 of laser controller 180 uses a first pulse rate when optical energy is to be used as an ablation therapy and a second pulse rate when pressure wave energy is to be used as an ablation therapy, the second pulse rate being different from the first pulse rate. In one embodiment, output logic 222 of laser controller 180 uses a first power level and a first pulse rate when optical energy is to be used as an ablation therapy and a second power level and a second pulse rate when pressure wave energy is to be used as an ablation therapy, the second power level being different from the first power level and the second pulse rate being different from the first pulse rate. In one embodiment, output logic 222 of laser controller 180 uses the same power level when optical energy is to be used as an ablation therapy and when pressure wave energy is to be used as an ablation therapy. In one embodiment, output logic 222 of laser controller 180 uses the same pulse rate when optical energy is to be used as an ablation therapy and when pressure wave energy is to be used as an ablation therapy. In one embodiment, output logic 222 of laser controller 180 uses the same power level and the same pulse rate when optical energy is to be used as an ablation therapy and when pressure wave energy is to be used as an ablation therapy.

Figure 6:
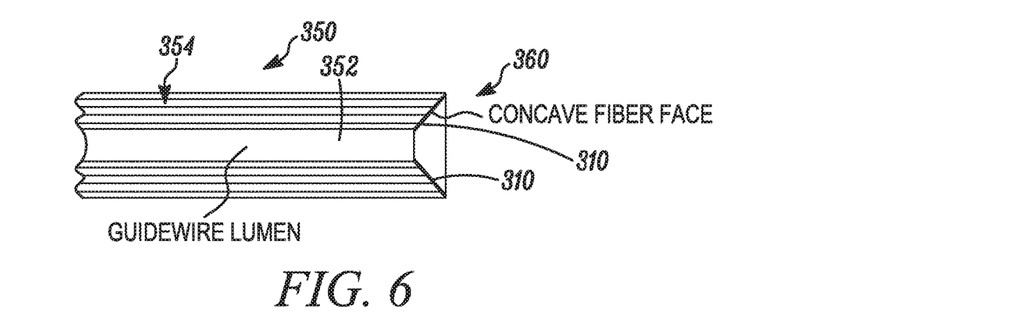
FIG. 6 illustrates an exemplary catheter construction including a plurality of transport members which surround a central lumen for a guide wire, the plurality of transport members providing a concave face.

FIG. 6 illustrates an exemplary laser catheter construction. A laser catheter 350 as shown in FIG. 6 includes a central lumen 352 which receives a guide wire (not shown). The transport member of laser catheter 350 is comprised of multiple transport members 354. In one embodiment, multiple transport members 354 are annular rings. In one embodiment, multiple transport members 354 are individual fiber optics. In one embodiment, a single transport member is provided. In the illustrative embodiment, the end face 360 of laser catheter 350 is a concave face. The polarized absorbing material 310 is not illustrated in FIGS. 6-11. In one embodiment, the polarized absorbing material 310 is a coating applied to the end of each transport member 354.

Figure 7:
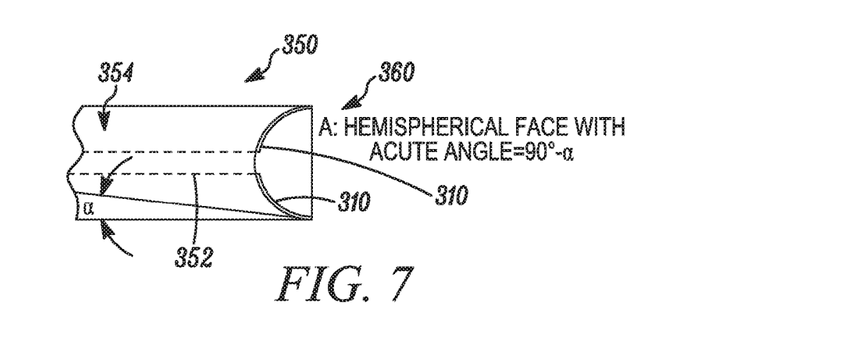
FIG. 7 illustrates another exemplary catheter construction having a hemispherical face with an acute angle.
Figure 8:
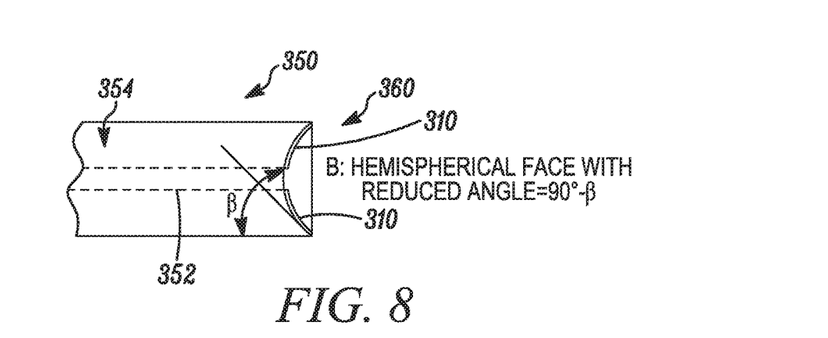
FIG. 8 illustrates another exemplary catheter construction having a hemispherical face with a reduced angle.
Figure 9:
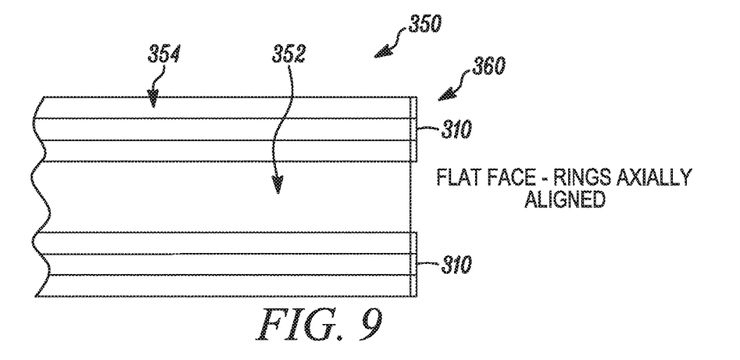
FIG. 9 illustrates the catheter construction of FIG. 6 wherein the plurality of transport members provide a linear face.
Figure 10:
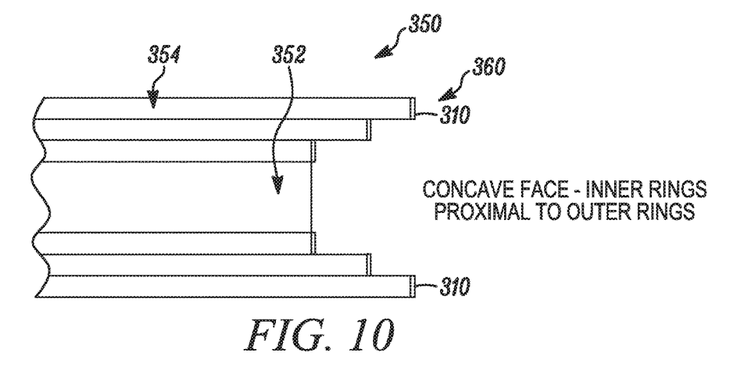
FIG. 10 illustrates the catheter construction of FIG. 6 wherein the plurality of transport members are offset axially to provide a stepped concave face, each of the transport members having a flat face.
Figure 11:
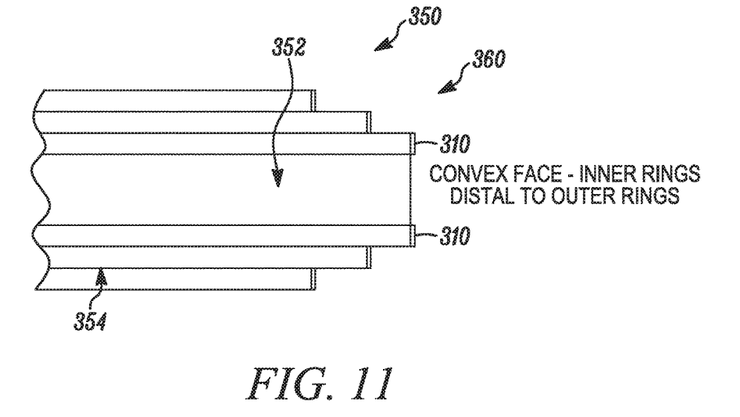
FIG. 11 illustrates the catheter construction of FIG. 6 wherein the plurality of transport members are offset axially to provide a stepped convex face, each of the transport members having a flat face.

FIG. 7 illustrates another exemplary laser catheter construction of laser catheter 350 having a hemispherical face 360 with an acute angle. FIG. 8 illustrates another exemplary catheter construction of laser catheter 350 having a hemispherical face 360 with a reduced angle. FIG. 9 illustrates laser catheter 350 wherein the plurality of transport members provide a linear face 360. FIG. 10 illustrates laser catheter 350 wherein the plurality of transport members are offset axially to provide a stepped concave face, each of the transport members having a flat face. FIG. 11 illustrates laser catheter 350 wherein the plurality of transport members are offset axially to provide a stepped convex face, each of the transport members having a flat face. In one embodiment, laser catheter 350 permits the movement of transport members 354 relative to each other. Thus, laser controller 180 may through a plurality of actuators move the individual transport members 354 to dynamically alter the effective shape of face 360. The changing of the shape of face 360 would alter the focusing of the energy communicated to the target site 232. Exemplary shapes of face 360 include continuous faces, step-wise faces, a linear face, a concave face, a convex face, a hemispherical face, a parabolic face, and other suitable geometries. In one embodiment, face 360 focuses the energy exiting laser catheter 350 on a central longitudinal axis of laser catheter 350. In one embodiment, face 360 focuses the energy exiting laser catheter 350 offset from a central longitudinal axis of laser catheter 350.

Figure 12:
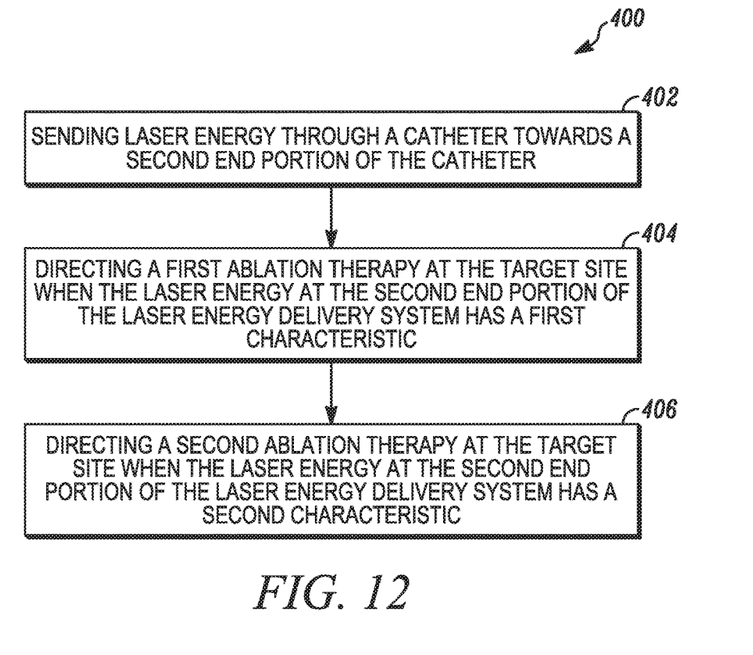
FIG. 12 illustrates an exemplary processing sequence of the laser controller.

Referring to FIG. 12, an exemplary processing sequence 400 of polarization module 212 of laser controller 108 is shown. Ablation system 100 sends laser energy through a catheter towards a second end portion of the catheter, as represented by block 402. Ablation system 100 directs a first ablation therapy at the target site when the laser energy at the second end portion of the laser energy delivery system has a first characteristic, as represented by block 404. Ablation system 100 directs a second ablation therapy at the target site when the laser energy at the second end portion of the laser energy delivery system has a second characteristic, as represented by block 406.

Figure 13:
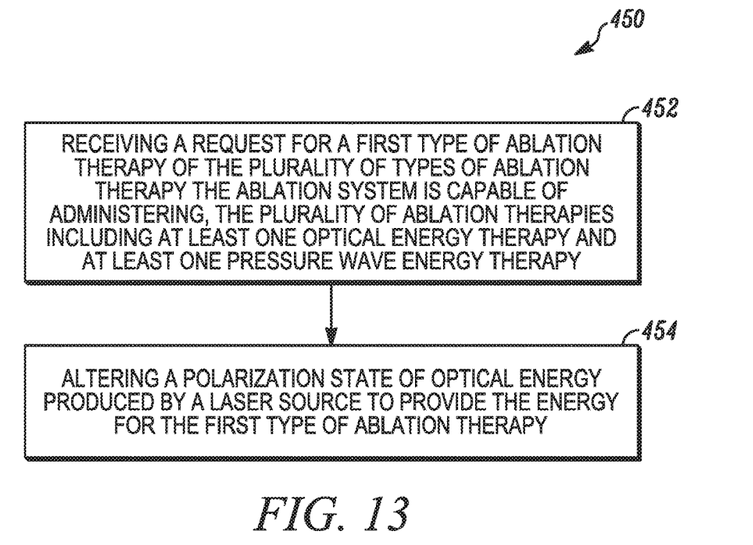
FIG. 13 illustrates another exemplary processing sequence of the laser controller.

Referring to FIG. 13, an exemplary processing sequence 450 of polarization module 212 of laser controller 108 is shown. Processing sequence 450 is for an ablation system capable of administering a plurality of types of ablation therapy, the plurality of ablation therapies including at least one optical energy therapy and at least one pressure wave energy therapy. Ablation system 100 receives a request for a first type of ablation therapy of the plurality of types of ablation therapy, as represented by block 452. In one embodiment the request is received through one of the input devices of the ablation system 100. Ablation system 100 alters a polarization state of optical energy produced by a laser source to provide the energy for the first type of ablation therapy, as represented by block 454. In one embodiment, the first type of ablation therapy is a pressure wave energy therapy. In one embodiment, the first type of ablation therapy is an optical energy therapy.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A catheter assembly for an ablation system, the catheter system receiving laser energy from a laser source, the catheter assembly comprising:
   a first transport member having a first proximal end and a first distal end surface;
   a second transport member disposed axially concentric relative to the first transport member, wherein the second transport member has a second proximal end and a second distal end surface, the second distal end surface and the first distal end surface being unaligned;
   a coupler positioned proximate the first proximal end of the first transport member and the second proximal end of the second transport member, the coupler adapted to couple laser energy from the laser source into the first transport member and the second transport member;
   at least one transducer coupled to the first distal end surface of the first transport member and the second distal end surface of the second transport member, wherein the at least one transducer passes the laser energy out of the catheter assembly as optical energy when the laser energy has a first polarization state and converts the laser energy to pressure wave energy when the laser energy has a second polarization state;
   a polarization module for controlling polarization state of the laser energy delivered to the at least one transducer, wherein the polarization module has a first setting wherein the polarization state of the laser energy delivered to the at least one transducer is the first polarization state and a second setting wherein the polarization state of the laser energy delivered to the at least one transducer is the second polarization state; and
   polarization logic for controlling the polarization module.

2. The catheter assembly of claim 1, wherein the at least one transducer absorbs laser energy with the second polarization state.

3. The catheter assembly of claim 1, wherein the first distal end surface of the first transport member is recessed relative to the second distal end surface of the second transport member.

4. The catheter assembly of claim 1, wherein the polarization module comprises a linear polarizer.

5. The catheter assembly of claim 1, wherein the polarization module comprises a circular polarizer.

6. The catheter assembly of claim 1, wherein the polarization module comprises an elliptical polarizer.

7. The catheter assembly of claim 1, wherein the polarization module comprises a wire grid polarizer.

8. The catheter assembly of claim 1, wherein the polarization module comprises a crystalline polarizer.

9. The catheter assembly of claim 1, wherein the polarization module comprises silver nanoparticles.

10. The catheter assembly of claim 1, wherein the polarization module comprises a beam splitter.

11. The catheter assembly of claim 1, wherein the polarization module comprises angle plates.

12. The catheter assembly of claim 1, wherein the polarization module comprises birefringent materials.

13. The catheter assembly of claim 1, wherein the polarization module comprises a liquid crystal.

14. The catheter assembly of claim 1, wherein the first transport member is an annular ring.

15. The catheter assembly of claim 14, wherein the annular ring is a first annular ring, and wherein the second transport member is a second annular ring.

16. The catheter assembly of claim 1, wherein the second transport member is an annular ring.

* * * * *